(12) United States Patent
Mitsuhashi et al.

(10) Patent No.: US 6,905,861 B2
(45) Date of Patent: Jun. 14, 2005

(54) D-AMINOACYLASES, METHOD FOR PRODUCING THE SAME, AND METHOD FOR PRODUCING D-AMINO ACIDS USING THE SAME

(75) Inventors: Kazuya Mitsuhashi, Ibaraki (JP); Hiroaki Yamamoto, Ibaraki (JP); Akinobu Matsuyama, Ibaraki (JP); Shinji Tokuyama, Shizuoka (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/242,378

(22) Filed: Sep. 10, 2002

(65) Prior Publication Data

US 2003/0113893 A1 Jun. 19, 2003

Related U.S. Application Data

(63) Continuation of application No. 09/361,901, filed on Jul. 27, 1999, now Pat. No. 6,514,742.

(30) Foreign Application Priority Data

Jul. 29, 1998 (JP) ........................................... 10/228636

(51) Int. Cl.$^7$ ................................................. C12N 9/78
(52) U.S. Cl. ..................................................... 435/227
(58) Field of Search ........................................ 435/227

(56) References Cited

U.S. PATENT DOCUMENTS

5,916,774 A    6/1999  Tokuyama ................. 435/71.2
6,030,823 A    2/2000  Tokuyama ................. 435/227

FOREIGN PATENT DOCUMENTS

| JP | 51-121591 | 10/1976 |
| JP | 62126976 | 6/1987 |
| JP | 5-328972 | 12/1993 |
| JP | 6-22776 | 2/1994 |

OTHER PUBLICATIONS

Moriguchi et al., "Production, Purification, and Characterization of D–Aminoacylase from Alcaligenes xylosoxydans subsp. xylosoxydans A–6" Biosci. Biotech. Biochem., vol. 57, No. 7, pp. 1149–1152, 1993.

Yang et al., "Characterization of D–Aminoacylase from Alcaligenes denitrificans DA181" Biosci. Biotech. Biochem. vol. 56, No. 9, pp. 1392–1395, 1992.

Sugie et al., "Purification and Properties of D–Aminoacylase of Streptomyces olivaceus" Agric. Biol. Chem., vol. 42, No. 1, pp. 107–113, 1978.

Sakai et al., "Purification and Properties of D–Aminoacylase from Alcaligenes denitrificans subsp. xylosoxydans MI–4" Journal of Fermentation and Bioengineering, vol. 71, No. 2, pp. 79–82, 1991.

Wakayama et al., "Cloning and Sequencing of a Gene Encoding . . . ," Bioscience Biotechnology Biochemistry, 59(11):2115–2119, 1995.

*Primary Examiner*—Rebecca Prouty
(74) *Attorney, Agent, or Firm*—Fish & Richardson P.C.

(57) ABSTRACT

D-aminoacylase derived from fungi is provided. The fungi capable of producing D-aminoacylase include those belonging to the genus Hypomyces, Fusarium, Auricularia, Pythium, and Menisporopsis. The fungal D-aminoacylase is useful for efficiently producing D-amino acids from N-acetyl-D-amino acids.

11 Claims, 5 Drawing Sheets

SEQUENCE LISTING

<160> NUMBER OF SEQ ID NOS: 5

<210> SEQ ID NO 1
<211> LENGTH: 25
<212> TYPE: PRT

-continued

```
<213> ORGANISM: Hypomyces mycophilus

<400> SEQUENCE: 1

Gly Phe Ile Leu Ser Pro Gly Phe Ile Asp Met His Ala His Ser Asp
 1               5                  10                  15

Lys Tyr Leu Leu Ser His Pro Thr His
                20                  25

<210> SEQ ID NO 2
<211> LENGTH: 20
<212> TYPE: PRT
<213> ORGANISM: Hypomyces mycophilus

<400> SEQUENCE: 2

Val Leu Ala Asp Glu Tyr Pro Gln Ala Phe Tyr Ala Pro His Ala Tyr
 1               5                  10                  15

Ser Arg Gly Phe
                20

<210> SEQ ID NO 3
<211> LENGTH: 18
<212> TYPE: PRT
<213> ORGANISM: Hypomyces mycophilus

<400> SEQUENCE: 3

Thr Ala Thr Asn Val Ala Met Leu Val Pro Gln Gly Asn Leu Arg Leu
 1               5                  10                  15

Leu Ala

<210> SEQ ID NO 4
<211> LENGTH: 18
<212> TYPE: PRT
<213> ORGANISM: Hypomyces mycophilus

<400> SEQUENCE: 4

Ile Gly Glu Pro Gly Ser Ile Ser His Asp Ser Ala Arg Arg Val Asp
 1               5                  10                  15

Ala Lys

<210> SEQ ID NO 5
<211> LENGTH: 20
<212> TYPE: PRT
<213> ORGANISM: Hypomyces mycophilus

<400> SEQUENCE: 5

Ser Tyr Thr Gly Arg Phe Val Gly Glu Ile Ala Arg Glu Thr Asn Arg
 1               5                  10                  15

Leu Pro Ile Glu
                20
```

D-AMINOACYLASES, METHOD FOR PRODUCING THE SAME, AND METHOD FOR PRODUCING D-AMINO ACIDS USING THE SAME

This application is a continuation of U.S. patent application Ser. No. 09/361,901, filed Jul. 27, 1999, now U.S. Pat. No. 6,514,742, which claims priority under 35 USC §119 to Japanese Patent Application Serial No. 10/228636, filed Jul. 29, 1998. These applications are incorporated herein by reference in their entirety.

FIELD OF THE INVENTION

The present invention relates to a D-aminoacylase produced by fungi, a method for producing said D-aminoacylase, and a method for producing D-amino acids using said D-aminoacylase.

BACKGROUND OF THE INVENTION

Enzymes have excellent catalytic functions with substrate specificity, reaction specificity, and stereospecificity. Stereospecificity of enzymes, with some exceptions, are nearly absolute.

Recent precise research has increased the importance of optically active substances for use in drugs, pesticides, feeds, and perfumes. Optical isomers sometimes have quite different biological activities. D(R)-form thalidomide has no teratogenic activity, but its L(S)-form shows strong teratogenicity. The practical use of thalidomide racemate caused the drug injury incidents. If one enantiomer shows an effective biological activity, the other enantiomer may sometimes have no activity, rather, it may competitively inhibit the activity of the effective enantiomer. In some cases, the activity of the racemate is reduced to half or less of the activity of the effective enantiomer. Accordingly, it is industrially important to obtain (synthesize or optically resolve) optically pure enantiomers. For this purpose, techniques for effective resolution of synthetic racemate have been widely used. Enzymatic optical resolution has drawn attention because it does not produce by-products and a bulk of liquid waste.

Generally, L-amino acids are widely and largely utilized in seasonings, food and feed additives, and infusions and are thus very highly demanded. L-Amino acids have been produced mainly by direct fermentation using microorganisms. Optical resolution is also a known method for producing L-amino acids by hydrolyzing N-acyl-DL-amino acids using L-aminoacylases. It has been utilized to industrially produce L-amino acids that are difficult to produce by fermentation. L-aminoacylases are widely found in animals, plants, and microorganisms. They have been purified from various organisms, and their properties have been clarified. N-terminal amino acids of many proteins are considered to be N-acetylated in vivo. L-Aminoacylases presumably regenerate N-acetyl-amino acids produced by decomposition of proteins to amino acids. Among L-aminoacylases, acylase, which acts on N-acyl-L-glutamic acid, is reportedly involved in arginine biosynthesis (Fruth, H., Leisinger, T.: J. Gen. Microb. 125, pp1 (1981)).

In contrast, D-amino acids have not been a subject of interest for a long time because they are nonprotein amino acids. D-amino acids were known to occur in small cyclic peptides, peptidoglycan of bacterial cell walls, and peptide antibiotics. However, D-amino acids have been demonstrated to be constituents of neuro peptides and to exist as binding forms in tooth enamel, the lens, and cerebral proteins, resulting in investigation of physiological significance and enzymatic synthesis of D-amino acids.

At present, DL-amino acids have been optically resolved by physicochemical, chemical, and enzymatic methods. The enzymatic methods are the most convenient and industrially applicable for, for example, continuously producing L-methionine from N-acetyl-DL-methionine using a bioreactor of immobilized L-aminoacylase. D-amino acids may also be produced using hydantoinase. The method consists of two-step enzymatic reactions. The first reaction uses D-specific hydantoinase to convert D,L-5-substituted-hydantoin, which is synthesized at low cost from aldehyde analogues, to a D-carbamyl derivative. The second reaction uses D-amino acid carbamylase.

Another method comprises hydrolyzing N-acetyl-DL-amino acids with D-aminoacylase to produce D-amino acids (Sugie, M. and Suzuki, H.: Argric. Biol. Chem. 44, pp1089 (1980), Tsai, Y. C., Lin, C. S., Tseng, T. H., Lee, H. and Wang, Y. J.: J. Enzyme Microb. Technol. 14, pp384 (1992)).

D-aminoacylase was first reported to be found in Pseudomonas sp. KT83 isolated from soil by Kameda et. al in 1952 (Kameda, Y., Toyoura, H., Kimura, Y. and Yasuda, Y.: Nature 170, pp888 (1952)). This enzyme hydrolyzed N-benzoyl derivatives of D-phenylalanine, D-tyrosine, and D-alanine. Thereafter, D-aminoacylases were derived from microorganisms belonging to the genus Pseudomonas (Kubo, K., Ishikura, T., and Fukagawa, Y.: J. Antibiot. 43, pp550 (1980), Kubo, K., Ishikura, T. and Fukagawa, Y.: J. Antibiot. 43, pp556 (1980), Kameda, Y., Hase, T., Kanatomo, S. and Kita, Y.: Chem. Pharm. Bull. 26, pp2698 (1978), Kubo, K., Ishikura, T. and Fukagawa, Y.: J. Antibiot. 43, pp543 (1980)), the genus Streptomyces (Sugie, M. and Suzuki, H.: Argric. Biol. Chem. 42, pp17 (1978), Sugie, M. and Suzuki, H.: Argric. Biol. Chem. 44, pp1089 (1980)), and the genus Alcaligenes (Tsai, Y. C., Tseng, C. P., Hsiao, K. M. and Chen, L. Y.: Appl. Environ. Microbiol. 54, pp984 (1988), Yang, Y. B., Hsiao, K. M., Li, H., Yano, Y., Tsugita, A. and Tsai, Y. C.: Biosci. Biotech. Biochem. 56, pp1392 (1992), Yang, Y. B., Lin, C. S., Tseng, C. P., Wang, Y. J. and Tsai, Y. C.: Appl. Environ. Microbiol. 57, pp2767 (1991), Tsai, Y. C., Lin, C. S., Tseng, T. H., Lee, H. and Wang: Microb. Technol. 14, pp384 (1992), Moriguchi, M. and Ideta, K.: Appl. Environ. Microbiol. 54, pp2767 (1988), Sakai, K., Imamura, K., Sonoda, Y., Kido, H. and Moriguchi, M.: FEBS, 289, pp44 (1991), Sakai, K., Obata, T., Ideta, K. and Moriguchi, M.: J. Ferment. Bioeng. 71, pp79 (1991), Sakai, K., Oshima, K. and Moriguchi, M.: Appl. Environ. Microbiol. 57, pp2540 (1991), Moriguchi, M., Sakai, K., Katsuno, Y., Maki, T. and Wakayama, M.: Biosci. Biotech. Biochem., 57, pp1145 (1993), Kayama, M., Ashika, T., Miyamoto, Y., Yoshikawa, T., Sonoda, Y., Sakai, K. and Moriguchi, M.: J. Biochem. 118, pp204 (1995)), Moriguchi, M., Sakai, K., Miyamoto, Y. and Wakayama, M.: Biosci. Biotech. Biochem., 57, pp1149 (1993)).

Tsai et al. and Moriguchi et al. also clarified the characteristics of D-aminoacylase derived from microorganisms belonging to the genera Alcaligenes and Pseudomonas and the amino acid and nucleotide sequences of the enzymes. Moriguchi et al. found that microorganisms belonging to the genera Alcaligenes and Pseudomonas produced three species of D-aminoacylase by using different inducers (Wakayama, M., Katsumo, Y., Hayashi, S., Miyamoto, Y., Sakai, K. and Moriguchi, M.: Biosci. Biotech. Biochem. 59, pp2115 (1995)).

Furthermore, Moriguchi et al. determined the nucleotide sequences of these D-aminoacylases derived from a microorganism belonging to the genus Alcaligenes and compared it with L-aminoacylases derived from *Bacillus stereothermophilus,* human, and pig. The result demonstrated that these D-aminoacylases have a low homology with L-aminoacylases (Wakayama, M., Katsuno, Y., Hayashi, S., Miyamoto, Y., Sakai, K. and Moriguchi, M.: Biosci. Biotech. Biochem., 59, pp2115 (1995)).

Sugie et al. reported D-aminoacylase of a microorganism belonging to the genus Streptomyces of actinomycetes (Sugie, M. and Suzuki, H.: Argric. Biol. Chem. 42, pp107 (1978), Sugie, M. and Suzuki, H.: Argric. Biol. Chem. 44, pp1089 (1980)). However, the enzyme has not been purified yet, and its characteristics remain unknown.

As described above, many D-aminoacylases have been isolated from bacteria and have been used to produce D-amino acids. However, the conventional methods for producing D-amino acids using bacteria have the following problems.

Most of the conventional bacterial D-aminoacylases are inducible enzymes, and N-acetyl-DL-amino acid is usually required for their production. The culture medium of the bacterium used for producing D-aminoacylase contains the unreacted N-acetyl-D-amino acid as well as the degradation product of D-amino acid. In order to react D-aminoacylase produced by these bacteria with a substrate other than N-acetyl-D-amino acid used as the enzyme inducer, it was necessary to isolate the cultured bacteria from the growth medium. Even when the enzyme reacts with N-acetyl-D-amino acid as the substrate, the bacteria must be removed to purify D-amino acid produced. A continuous centrifuge, such as a Westfalia centrifuge, and a Sharples centrifuge were usually used to remove the cultured bacteria. One problem of the centrifugation is that it takes longer to centrifuge a large volume of the culture medium, often causing the inactivation of D-aminoacylase during centrifugation. Furthermore, the bacteria and actinomycetes lyse as the reaction proceeds and thus are difficult to separate centrifugation. As described above, D-amino acids are not always efficiently produced using the conventional bacterial D-aminoacylase.

SUMMARY OF THE INVENTION

An objective of the present invention is to provide an efficient method for producing D-amino acids using microorganisms other than the conventional bacteria and actinomycetes.

In order to solve the above-described problems, the present inventors have attempted to produce D-amino acids using fungi which are eukaryotic cells sharing a common cell structure and many chemical properties and functions with animals and plants (eukaryotic characteristics). Fungi are advantageous in that: (1) Fungal cells are large and filamentous and thus can be readily collected by filtration from the liquid culture; (2) fungi efficiently utilize carbohydrates and are able to grow more rapidly than usual at a high carbon/nitrogen ratio, reducing the cost of fermentation materials per unit of enzyme; (3) fungi can be economically cultured in a solid culture (i.e., without a liquid culture) since they grow under natural aeration conditions; this translates into less investment in equipment, high concentration enzyme production, and less organic solvents to extract enzymes; (4) fungi are able to grow well in the solid culture with a low active water level, which can prevent contamination with bacteria that grow poorly in a low active water level; and (5) most fungi efficiently utilize starch, cellulose, and proteins, including inexpensive nutrient sources such as cassava as a starch source, wheat bran, rice, rice bran, barley, wheat, soybean, and cellulose sources.

No fungi producing D-aminoacylase has been reported so far. The present inventors first screened D-aminoacylase-producing fungi and found that many fungi belonging to the genera Hypomyces, Fusarium, Auricularia, Pythium, and Menisporopsis can produce D-amino acid from N-acetyl-D-amino acid. These fungi thus have D-aminoacylase activity.

The present inventors then succeeded in isolating and purifying D-aminoacylases from fungi with D-aminoacylase activity by salting-out with ammonium sulfate and various chromatographies. Furthermore, the inventors studied various physico-chemical properties of the purified D-aminoacylases such as their substrate specificity and thermostability, confirming that D-amino acid can be efficiently produced by reacting the fungal D-aminoacylases with N-acetyl-D-amino acid under the appropriate conditions.

The present inventors are the first to discover D-aminoacylase in eukaryotes, fungi. The enzyme had been found only in prokaryote bacteria and actinomycetes. The fungal D-aminoacylase can be used to produce D-amino acids.

Accordingly, the present invention relates to a D-aminoacylase produced by fungi, a method for producing said D-aminoacylase, and a method for producing D-amino acids using said D-aminoacylase.

More specifically, the present invention provides a D-aminoacylase derived from a fungus.

In another aspect, the invention provides a D-aminoacylase having physico-chemical properties (a) through (f) below:

(a) function: the enzyme acts on N-acetyl-D-amino acids to produce corresponding D-amino acids;

(b) molecular weight: the molecular weight of the enzyme is about 64,000 daltons determined by SDS-polyacrylamide gel electrophoresis, and about 56,000 daltons determined by gel filtration chromatography on Superdex 200 Hi-Load 6/16 (Amersham Pharmacia Biotech)

(c) substrate specificity: the enzyme acts on N-acetyl-D-tryptophan, N-acetyl-D-phenylalanine, N-acetyl-D-valine, N-acetyl-D-leucine, and N-acetyl-D-methionine, but not on N-acetyl-L-tryptophan, N-acetyl-L-phenylalanine, N-acetyl-L-valine, N-acetyl-L-leucine, or N-acetyl-L-methionine;

(d) thermostability: when heated at pH 9.5 for 30 min, the enzyme is stable at 45° C., but inactivated at 60° C. or higher;

(e) optimal temperature: for the reaction at pH 7.5, the enzyme activity is optimal at about 45° C.; and (f) stabilizer: the enzyme activity is stabilized by reducing agents and activated by $ICH_2CONH_2$.

The present invention also provides a DNA encoding D-aminoacylase described above.

Furthermore, the invention provides a method for producing D-amino acids, wherein said method comprises reacting a fungus producing D-aminoacylase or D-aminoacylase derived from a fungus with N-acyl-DL-amino acid or its salt represented by the formula (I):

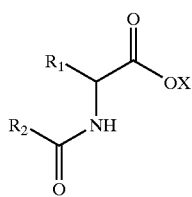

(I)

where $R_1$ and $R_2$ may be identical or different and each represents a hydrogen atom or a substituted or unsubstituted hydrocarbon group, provided that $R_2$ does not represent a hydrogen atom; and X is H, $NH_4$, or a metal ion.

Moreover, the invention provides a method for producing D-aminoacylase, wherein said method comprises culturing a fungus.

DETAILED DESCRIPTION OF THE INVENTION

Figure 1:
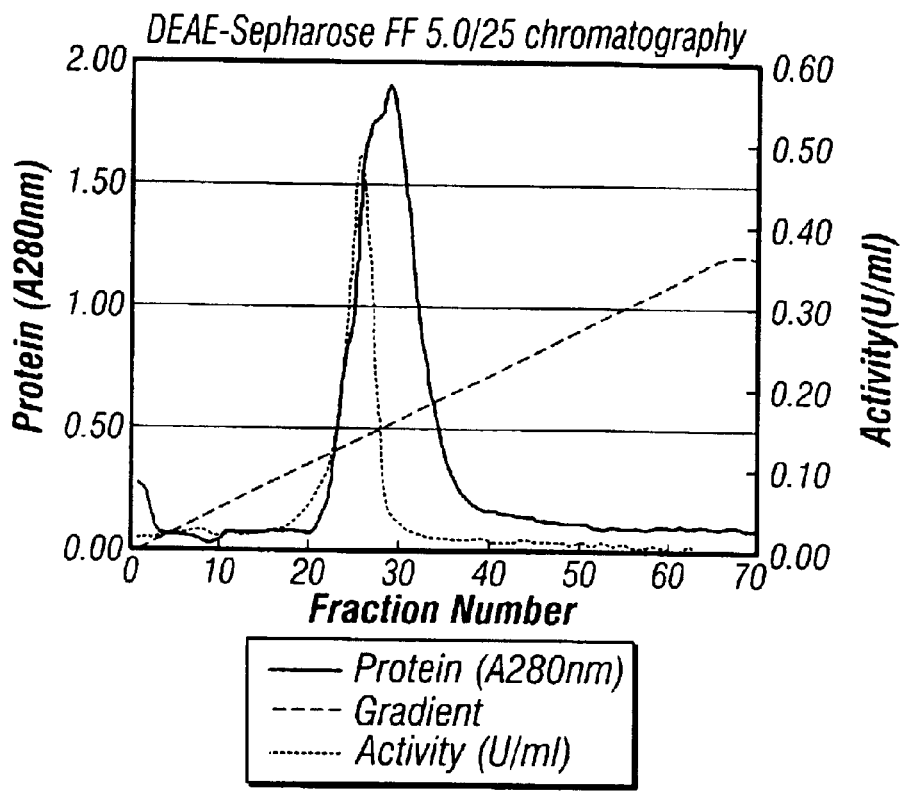
FIG. 1 shows the purification of the D-aminoacylase of the present invention by DEAE-Sepharose FF 5.0/25 anion exchange chromatography.

"D-aminoacylase" used herein means an enzyme reacting with an N-acyl-D-amino acid to catalyze the production of an organic acid and a D-amino acid.

D-Aminoacylase derived from fungi of the present invention can be produced by culturing fungi to allow them produce it. D-aminoacylase-producing fungi used in the present invention are not particularly limited as long as they are capable of producing D-aminoacylase. Fungi capable of producing D-aminoacylase include those belonging to the genera Hypomyces, Fusarium, Auricularia, Pythium, and menisporopsis, but are not limited to them.

Examples of the fungi belonging to the genus Hypomyces include the species *Hypomyces aurantius, Hypomyces broomeanus, Hypomyces chrysospermus, Hypomyces rosellus, Hypomyces sepulcralis, Hypomyces subiculosus,* and *Hypomyces mycophilus.* The fungi belonging to the genus Fusarium include the species *Fusarium solani.* The fungi belonging to the genus Auricular include the species *Auricular auriculajudae.* The fungi belonging to the genus Pythium include the species *Pythium aphanidermaatum.* The fungi belonging to the genus Menisporopsis include the species *Menisporopsis novaezelandiae.* However, fungi to be used are not limited to these species.

More specifically, D-aminoacylase can be derived from *Hypomyces aurantius* IFO 6847, *Hypomyces broomeanus* IFO 9164, *Hypomyces rosellus* IFO 6911, *Hypomyces chrysospermus* IFO 6817, *Hypomyces sepulcralis* IFO 9102, *Hypomyces subiculosus* IFO 6892, *Hypomyces mycophilus* ATCC 76474 or IFO 6785, *Fusarium solani* IFO 9974 or IFO 9975, *Auricularia auriculajudae* IFO 5949, *Pythium aphanidermaatum* IFO 7030, or *Menisporopsis novaezelandiae* IFO 9179. However, fungi to be used are not limited to these strains.

The above microorganisms with IFO numbers are recited in the List of Cultures 10th edition (1996) published by Institute of Fermentation Research, Osaka (IFO) and are available from IFO. The above microorganisms with ATCC numbers are recited in ATCC™ Catalogue on CD 1995 edition provided by "American Type Culture Collection (ATCC)" and are available from ATCC.

D-aminoacylase-producing fungi can be cultured using conventional fermentation techniques. Either synthetic or natural media can be used as long as they contain proper amounts of the carbon source, nitrogen source, inorganic materials, and other nutrients. The culture media may be either liquid or solid. More specifically, considering the planned utilization of the fungi, examples of the carbon source include sugars such as glucose, fructose, maltose, galactose, starch, starch hydrolyzate, molasses, and blackstrap molasses; natural products such as wheat, barley, and corn; alcohols such as glycerol, methanol, and ethanol; aliphatic hydrocarbons such as acetic acid, gluconic acid, pyruvic acid, and citric acid; hydrocarbons such as normal paraffin; and amino acids such as glycine, glutamine, and asparagine. One or more of the above carbon sources are used depending on assimilability of the fungus used. Examples of the nitrogen sources include organic nitrogen-containing compounds such as meat extract, peptone, yeast extract, soybean hydrolyzate, milk casein, casamino acid, various amino acids, corn steep liquor, and other hydrolyzates of animals, plants and microorganisms; and inorganic nitrogen-containing compounds such as ammonia, ammonium salts such as ammonium nitrate, ammonium sulfate, ammonium chloride, nitrates such as sodium nitrate, and urea. One or more of the above nitrogen sources are used depending on assimilability of the fungus.

For fungi to efficiently produce D-aminoacylase, N-acetyl-DL-amino acid can be used as the enzyme inducer depending upon the fungus employed.

Furthermore, a minute amount of one or more inorganic salts can be used. Examples thereof include phosphates; hydrochlorides; nitrates; acetates; or similar salts of magnesium, manganese, potassium, calcium, sodium, copper, or zinc. Antifoaming agents, such as vegetable oil, surfactants, or silicon, may be added to the culture medium.

Culturing can be performed in the liquid medium containing the above-described ingredients using the usual culture methods, such as shake culturing, aeration agitation culturing, continuous culturing, or fed-batch culturing.

Culturing conditions may be properly selected depending upon the fungal strain and culture method, and are not particularly limited as long as the fungi used can proliferate to produce D-aminoacylase. It is usually preferred to adjust the initial pH to 4 to 10, preferably 6 to 8, and to culture at a temperature of 15 to 50° C., preferably 25 to 35° C. The culturing time is also not particularly limited as long as a sufficient amount of fungal cells having the D-aminoacylase activity can be obtained. The culturing is usually performed for 1 to 14 days, preferably for 1 to 3 days. D-Aminoacylase produced and accumulated in the culture can be recovered and isolated by the following methods.

When D-aminoacylase is intracellularly produced, the fungal cells are collected by filtration or centrifugation after the culturing and washed with buffer, physiological saline, etc. The enzyme can then be extracted by disrupting the fungal cells using physical means such as freeze-thawing, ultrasonication, compression, osmotic treatment, or trituration; using biochemical means such as cell wall lysis with lysozyme; or using chemical means such as surfactant treatment. One or more of these treatments can be combined. The crude D-aminoacylase thus obtained can be purified by a single or combined fractionation means including salting out; fractional precipitation with organic solvents; various chromatographies such as salting-out chromatography, ion-exchange chromatography, gel filtration chromatography, hydrophobic chromatography, dye chromatography, hydroxyl apatite chromatography, or affinity chromatography; and electrophoresis such as isoelectric focusing and native electrophoresis. The above chromatographies can be performed using open columns or by means of medium-pressure or high-performance liquid chromatography (HPLC).

For example, the fungal cells collected by filtration are freeze-thawed and triturated using a Dyno Mill to obtain a D-aminoacylase extract. The extract is then successively subjected to salting-out using ammonium sulfate, ion-exchange chromatography on DEAE-Sepharose FF, hydrophobic chromatography on Phenyl-Sepharose FF, Sephadex 200 gel filtration chromatography, or MonoQ ion-exchange chromatography. The enzyme thus purified can be detected as a single protein band on the SDS-polyacrylamide gel electrophoresis.

The fungal D-aminoacylase of the present invention has the physico-chemical properties (a) through (f) below:
(a) function: the enzyme acts on N-acetyl-D-amino acids to produce corresponding D-amino acids;
(b) molecular weight: the molecular weight of the enzyme is about 64,000 daltons determined by SDS-polyacrylamide gel electrophoresis, and about 56,000 daltons determined by gel filtration chromatography on Superdex 200 Hi-Load 6/16 (Amersham Pharmacia Biotech);
(c) substrate specificity: the enzyme acts on N-acetyl-D-tryptophan, N-acetyl-D-phenylalanine, N-acetyl-D-valine, N-acetyl-D-leucine, and N-acetyl-D-methionine, but not on N-acetyl-L-tryptophan, N-acetyl-L-phenylalanine, N-acetyl-L-valine, N-acetyl-L-leucine, or N-acetyl-L-methionine;
(d) thermostability: when heated at pH 9.5 for 30 min, the enzyme is stable at 45° C., but inactivated at 60° C. or higher;
(e) optimal temperature: for the reaction at pH 7.5, the enzyme activity is optimal at about 45° C.; and
(f) stabilizer: the enzyme activity is stabilized by reducing agents and activated by $ICH_2CONH_2$.

The D-aminoacylase of the present invention having the above properties is preferably derived from fungi belonging to the genus Hypomyces, more preferably the species *Hypomyces mycophilus*, and still more preferably *Hypomyces mycophilus* ATCC 76474 or IFO 6785 strain. The enzyme may contain the amino acid sequences described in SEQ ID Nos: 1 through 5.

D-aminoacylase of the present invention is capable of acting on various N-acyl-D-amino acids to yield the corresponding D-amino acids, enabling the industrially advantageous production of D-amino acids using said enzyme. For example, D-amino acid can be selectively produced by reacting D-aminoacylase of this invention with N-acyl-DL-amino acid, a mixture of D- and L-enantiomers.

N-acyl-DL-amino acids used in the present invention are not particularly limited and can be selected from a wide variety of compounds. A typical N-acyl-DL-amino acid can be represented by the formula (I):

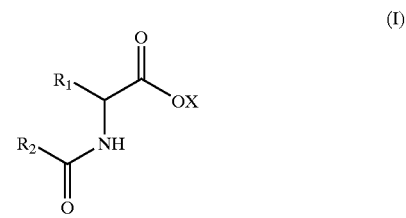

(I)

where $R_1$ and $R_2$ may be identical or different and each represents a hydrogen atom or a substituted or unsubstituted hydrocarbon group, provided that $R_2$ does not represent a hydrogen atom; and X is H, $NH_4$, or a metal ion.

The hydrocarbon group represented by $R_1$ and $R_2$ is preferably alkyl, alkenyl, alkynyl, cycloalkyl, aryl, or aralkyl, which may be substituted. More specifically, the hydrocarbon group includes linear or branched alkyl such as methyl, ethyl, n-propyl, i-propyl, n-butyl, i-butyl, sec-butyl, t-butyl, n-pentyl, i-pentyl, n-hexyl, etc.; alkenyl such as ethenyl, 1-propenyl, 2-propenyl, 1-butenyl, 2-butenyl, 2-pentenyl, 4-pentenyl, 1-hexenyl, 3-hexenyl, 5-hexenyl, etc.; alkynyl such as ethynyl, 1-propynyl, 2-pentynyl, etc.; aryl such as phenyl, naphthyl, etc.; cycloalkyl such as cyclopropyl, cyclobutyl, cyclopentyl, cyclohexyl, etc. The substituent of the hydrocarbon group for $R_1$ and $R_2$ includes halogen; alkyl as defined above; alkenyl as defined above; alkynyl as defined above; aryl as defined above; heterocyclic such as piridyl, indole, quinolyl, etc.; amino; hydroxyl; thio; etc. $R_1$ is preferably indolyl (N-acyl-DL-tryptophan), benzyl (N-acyl-DL-phenylalanine), thiomethylethyl (N-acyl-DL-methionine), isopropyl (N-acyl-DL-valine), or 2-methylpropyl (N-acyl-DL-leucine). $R_2$ is preferably methyl, chloromethyl, phenyl, or aminomethyl, which may be substituted with the above substituent(s). The metal ion represented by X includes sodium, patassium, etc. Preferable examples of N-acyl-DL-amino acids are N-acetyl-DL-amino acids such as N-acetyl-DL-methionine, N-acetyl-DL-valine, N-acetyl-DL-tryptophan, N-acetyl-DL-asparagine, N-acetyl-DL-phenylalanine, N-acetyl-DL-alanine, and N-acetyl-DL-leucine.

N-acetyl-DL-amino acids can be used in the form of a salt such as a sodium salt or a potassium salt.

D-Aminoacylase used for producing D-amino acid in the present invention includes a partially purified enzyme as well as the purified one. The enzyme also includes a recombinant protein obtained by isolating a DNA encoding D-aminoacylase, introducing said DNA into suitable host cells, and allowing the cells to express the enzyme. A DNA encoding D-aminoacylase can be isolated, for example, by obtaining the purified enzyme, determining its partial amino acid sequence, designing suitable oligonucleotide primers based on said determined amino acid sequence, and performing the polymerase chain reaction using the primers and, as a templete, the mRNA, cDNA, or genomic DNA prepared from the fungus from which the purified enzyme is derived.

Besides these enzymes, the D-aminoacylase-producing fungal cells themselves can also be used in the present invention. Namely, D-amino acid can be produced by directly reacting the fungus capable of producing D-aminoacylase with N-acetyl-DL-amino acid. The fungus can be used in the form of the culture medium, cells separated from the culture medium by centrifugation or the like, or cells resuspended in buffer, water, or the like after they are separated by centrifugation and washed. The separated cells can be used in a state as they are recovered, as their disrupts, as treated with acetone or toluene, or as lyophilizate.

D-aminoacylase or the fungus capable of producing said enzyme is reacted with N-acyl-D-amino acid under conditions suitable for the activity and stability of D-aminoacylase, and for the reactivity of the fungus. Some D-aminoacylases are activated by metal ions such as $Co^{2+}$ and $Ca^{2+}$. When such enzymes are used, the divalent metal ions may be added to the reaction solution. If the enzyme is inhibited by divalent metal ions, a chelating reagent such as EDTA can be added. Though the concentration of the substrate, N-acetyl-DL-amino acid, is not particularly limited, it is usually employed at a concentration of about 0.1 to 30 w/v%. Use of a large amount of D-aminoacylase often accelerates the reaction rate, and the enzyme is usually used in the amount of about 1 to 1,000 U/ml. One unit of the enzyme is defined as the amount of the enzyme to produce 1 μmol of D-tryptophan at 30° C. in 1 min when the enzyme is reacted with N-acetyl-D-tryptophan as the substrate. It is preferred to maintain the reaction temperature at which the D-aminoacylase activity is exhibited, 30 to 50° C. It is preferred to maintain the reaction pH at which the D-aminoacylase is active, for example, pH4 to 10. The reaction can be performed with or without stirring.

The enzyme or the fungus can often be stabilized by immobilization. It can be immobilized by a known method on a suitable carrier such as polyacrylamide gel, sulfur-containing polysaccharide gel (carrageenan gel), alginic acid gel, or agar gel.

The D-amino acids produced can be recovered from the reaction mixture by a known method such as direct crystallization by concentration or isoelectric precipitation, ion exchange resin treatment, membrane filtration, or the-like.

For example, D-tryptophan produced using N-acetyl-DL-tryptophan as a substrate can be purified as follows. After the enzymatic reaction, the reaction mixture is contacted with strongly acidic cation exchange resin to adsorb D-tryptophan. The resin was washed with water and eluted with 0.5 N aqueous ammonia. After the eluate was concentrated, the thus-obtained crude crystalline powder of D-tryptophan is dissolved in a small amount of 50% hot ethanol, decolorized with activated charcoal, and cooled to obtain purified crystals of D-tryptophan.

In the method of the present invention, D-valine can be purified as follows. After the enzymatic reaction, the microbial cells are removed by centrifugation or the like, and the resulting supernatant is adjusted to pH 1 by adding 6N hydrochloric acid. The precipitated N-acetyl-L-valine is removed by centrifugation. The supernatant is treated with activated charcoal, adjusted to pH 7.0, then added to an $H^+$-type strongly acidic cation exchanger (Amberlite IR-120B). Elution is performed with 5% aqueous ammonia, and the resulting eluate is dried at 80° C. under reduced pressure, thereby producing D-valine.

The present invention will be described in more detail with reference to the following examples but is not to be construed to be limited thereto.

In the following examples, "%" for concentration denotes weight per volume percent unless otherwise specified.

EXAMPLE 1

A platinum loopful of *Hypomyces aurantius* IFO 6847 strain, *Hypomyces broomeanus* IFO 9164 strain, *Hypomyces rosellus* IFO 6911 strain, *Hypomyces chrysospermus* IFO 6817 strain, *Hypomyces sepulcralis* IFO 9102 strain, *Hypomyces subiculosus* IFO 6892 strain, *Hypomyces mycophilus* ATCC 76474 or IFO 6785 strain, or *Fusarium solani* IFO 9974 or IFO 9975 strain was inoculated into 25 ml of YM medium (containing 0.3% yeast extract, 0.3% malt extract, 0.5% peptone, and 2.0% glucose, pH 6.0) in a 500-ml shouldered flask. The fungi were shake-cultured at 24° C. for 3 days. After culturing, a 5-ml aliquot of the culture medium was centrifuged in a refrigerated centrifuge to collect the fungal cells. The cells were washed with physiological saline solution (5 ml) and collected by centrifugation again. A reaction solution (containing 0.1% N-acetyl-D-amino acid shown in Table 1 below in Tris-HCl buffer, pH 7.5) was then added to the cells thus collected. The mixture was incubated in a 5-ml test tube with shaking at 30° C. for 24 hours.

D-Amino acid thus produced was determined by high-performance liquid chromatography (column, CROWNPAK CR (Daicel Chemical); column temperature, 26° C.; cooled in ice for only valine; mobile phase, $HClO_4$ aqueous solution, pH 2.0; flow rate, 1 ml/min; and detection, 200 nm). The results-are shown in Table 1.

TABLE 1

|  | D-Tryptophan produced from N-acetyl-D-tryptophan (mg/ml) | D-Methionine produced from N-acetyl-D-methionine (mg/ml) | D-Phenyl-alanine produced from N-acetyl-D-phenyl-alanine (mg/ml) | D-Veline produced from N-acetyl-F-valine (mg/ml) | D-Leucine produced from N-acetyl-D-leucine (mg/ml) |
|---|---|---|---|---|---|
| *Hypomyces aurantius* IFO 6847 | 0.008 | 0.02 | 0.005 | 0.14 | 0 |
| *Hypomyces broomeanus* IFO 9164 | 0.002 | 0.01 | 0.004 | 0.18 | 0 |

TABLE 1-continued

|  | D-Tryptophan produced from N-acetyl-D-tryptophan (mg/ml) | D-Methionine produced from N-acetyl-D-methionine (mg/ml) | D-Phenyl-alanine produced from N-acetyl-D-phenyl-alanine (mg/ml) | D-Veline produced from N-acetyl-F-valine (mg/ml) | D-Leucine produced from N-acetyl-D-leucine (mg/ml) |
|---|---|---|---|---|---|
| *Hypomyces chrysospermus* IFO 6817 | 0.001 | 0.12 | 0.003 | 3.16 | 1.05 |
| *Hypomyces rosellus* IFO 6911 | 0.08 | 0.14 | 0.06 | 2.73 | 0.3 |
| *Hypomyces sepulcralis* IFO 9102 | 0.01 | 0.24 | 0.15 | 3.19 | 1.60 |
| *Hypomyces subiculosus* IFO 6892 | 0.002 | 0.03 | 0.05 | 0.23 | 0.10 |
| *Hypomyces mycophilus* ATCC 76474 | 0.27 | 0.10 | 0.003 | 0.11 | 0.11 |
| *Hypomyces mycophilus* IFO 6785 | 0.40 | 0.71 | 0.65 | 0.98 | 0.55 |
| *Fusarium solani* IFO 9974 | 0 | 0.04 | 0.001 | 0 | 0.14 |
| *Fusarium solani* IFO 9975 | 0.001 | 0.02 | 0.002 | 0.22 | 0.21 |

From Table 1, it is clear that the D-aminoacylase producing capability was found in all fungal strains tested.

EXAMPLE 2

A platinum loopful of *Hypomyces rosellus* IFO 6911 strain, *Hypomyces sepulcralis* IFO 9102 strain, or *Hypomyces mycophilus* IFO 6785 strain was inoculated into 25 ml of YM medium (containing 0.3% yeast extract, 0.3% malt extract, 0.5% peptone, and 2.0% glucose; pH 6.0) in a 500-ml shouldered flask. The fungi were shake-cultured at 24° C. for 3 days. After culturing, a 5-ml aliquot of the culture medium was centrifuged in a refrigerated centrifuge to collect the fungal cells. The cells were washed with physiological saline solution (5 ml), and collected by centrifugation again. A reaction solution (containing 0.1% N-acetyl-DL-amino acid shown in Table 2 below in Tris-HCl buffer, pH 7.5) was added to the cells thus collected. The mixture was incubated in a 5-ml test tube with shaking at 30° C. for 24 hours. D-Amino acid thus produced was assayed by high-performance liquid chromatography (column, CROWNPAK CR (Daicel Chemical); column temperature, 26° C.; mobile phase, $HClO_4$ aqueous solution pH 2.0; flow rate, 1 ml/min; and detection, 200 nm) and examined for the optical purity. The results are shown in Table 2.

TABLE 2

|  | D-Tryptophan produced from N-acetyl-DL-tryptophan (mg/ml) | Optical purity of D-tryptophan (% ee) | D-Phenyl-alanine produced from N-acetyl-DL-phenylalanine (mg/ml) | Optical purity of D-phenyl-alanine (% ee) |
|---|---|---|---|---|
| *Hypomyces rosellus* IFO 6911 | 0.24 | 75 | 0.21 | 95 |
| *Hypomyces sepulcralis* IFO 9102 | 0.13 | 94 | 0.12 | 94 |
| *Hypomyces mycophilus* IFO 6785 | 0.10 | 37 | 0.16 | 40 |

It was thus confirmed that all the strains tested produced the D-enantiomer of a high optical purity from the corresponding DL-racemate.

EXAMPLE 3

*Auricularia auriculajudae* IFO 5949, *Pythium aphanidermaatum* IFO 7030, and *Menisporopsis novaezelandiae* IFO 9179 were each inoculated into sterilized media (100 ml each) (Czapek Dox Broth for IFO 5949, YM1 medium for IFO 7030, and POTATO DEXTROSE BROTH for IFO 9179) in 500-ml Erlenmeyer flasks. The fungi were cultured on a rotary shaker at 210 rpm at 24° C. for 7 days and collected by centrifugation using a HIMAC SCR 20B HITACHI centrifuge with a RPR10-2 rotor at 8,000 rpm (12,500× g) for 20 min. The cells thus sedimented were washed with 50 mM phosphate buffer (pH 7.0), dehydrated, and stored frozen.

In this experiment, POTATO DEXTROSE BROTH (DIFCO) was prepared by dissolving 24 g of the dried medium powder (a 10:1 mixture of Potato infusion form and Bacto Dextrose) in 1 liter of water, adding N-acetyl-DL-methionine (N—Ac—DL—Met) thereto to 0.1%, and adjusting the pH to 5.1. Czapek Dox Broth consisted of 0.3% $NaNO_3$, 0.1% $K_2HPO_4$, 0.05% $MgSO_4 \cdot 7H_2O$, 0.05% KCl, 0.001% $FeSO_4 \cdot 7H_2O$, 3.0% sucrose, 0.2% yeast extract, 0.2% polypeptone, and 0.1% N—Ac—DL—Met, and was adjusted to pH 7.3. YM1 medium (Yeast extract-malt extract-peptone-glucose medium) consisted of 0.5% polypeptone, 0.3% yeast extract, 0.3% malt extract, 0.2% glucose, and 0.1% N—Ac—DL—Met, and was adjusted to pH 5.5 to 6.0.

The frozen cells were disrupted by adding 50 mM phosphate buffer (pH 7.0) to the cells to give a cell suspension of 1 g of cells per 6 ml, putting the suspension (1.5 ml) and glass beads (0.2 dia. to 0.5 mm) (1.5 g) in a 2.0-ml sample vial equipped with a disrupter, and disrupting using a Mini-Bead Beater™ (BIOSPEC PRODUCTS) at 2,500 rpm for 150 sec followed by 3.5-min intervals of ice-cooling (a total of eight cycles). Disrupted cells thus obtained were centrifuged using a HIMAC SCR20B HITACHI centrifuge with a RPR20-2 rotor at 17,500 rpm (38,000×g) for 30 min at 4° C. to obtain the supernatant as the crude enzyme. The reaction was performed in a solution (containing 20 mM N—Ac—D-amino acid shown in Table 3, 1 mM $CoCl_2$, 50 mM phosphate buffer; pH 7.0) to assay the enzyme activity for each substrate. The results are shown in Table 3.

TABLE 3

| Substrate | Auricularia auriculajudae IFO 5949 | Pythium aphanidermaatum IFO 7030 | Menisporopsis novaezelandiae IFO 9179 |
|---|---|---|---|
| N-Acetyl-D-methionine | 2.45 | 0.90 | 0.89 |
| N-Acetyl-D-alanine | 1.46 | 0.29 | 0.09 |
| N-Acetyl-D-leucine | 2.68 | — | — |
| N-Acetyl-D-phenylalanine | 4.34 | — | 0.44 |
| N-Acetyl-D-tryptophan | 2.44 | — | 1.30 |
| N-Acetyl-D-valine | 3.33 | — | 0.16 |
| N-Acetyl-D-aspartic acid | 1.10 | — | 0.66 |

Figures in the table denote the amount (mM) of D-amino acids produced from the corresponding N-acetyl-D-amino acids. The D-aminoacylase activity was detected in all the strains tested, producing D-amino acid from the corresponding N-acetyl-D-amino acid.

EXAMPLE 4

(1) Fungal Strain and Flask Culture Method

YM medium (50 ml) (containing 0.3% yeast extract (Kyokuto Seiyaku), 0.3% malt extract (Kyokuto Seiyaku), 0.5% polypeptone (Nihon Seiyaku), 2.0% glucose (Wako Pure Chemical); pH 6.0) was placed in a 500-ml baffled Erlenmeyer flask, autoclaved, and used as the growth medium for producing D-aminoacylase by *Hypomyces mycophilus* IFO 6785 strain. The fungal strain previously grown in YM agar medium (containing 0.3% yeast extract, 0.3% malt extract, 0.5% polypeptone, 2.0% glucose (Wako Pure Chemical), and 1.5% agar (Wako Pure Chemical); pH 6.0) on the plate was excised in about 5-cm square sections using a sterilized surgical knife, inoculated into the above-described medium in the flask, and incubated on a rotary shaker at 145 rpm and 25° C. for 96 h. After incubation, the cells were collected by centrifugation (with a TOMY SEIKO MRX-150 centrifuge using a TMA-3 rotor) at 12,000 rpm (12,000×g) and 4° C. for 5 min. The cells thus collected were washed with physiological saline solution and centrifuged again using the same rotor at 12,000 rpm (12,000×g) for 5 min to obtain the cells.

(2) Assay Method for D-aminoacylase Activity

The cells obtained above were disrupted in 50 mM Tris-HCl (pH 7.5) containing 0.01% 2-ME (β-mercaptoethanol) and 1 mM PMSF (phenyl methyl sulfonyl fluoride) using a Mini Bead Beater 8 (BIOSPEC PRODUCTS) twice for 5 min each, then centrifuged at 15,000 rpm (18,000×g) for 5 min with an MRX-150 centrifuge using a TMA-2 rotor (TOMY SEIKO) to obtain the supernatant, a crude D-aminoacylase solution.

The enzyme reaction was performed in a reaction system (total volume 1.0 ml) containing 20 mM N-acetyl-D-tryptophan (Sigma), 50 mM Tris-HCl (pH 7.5), and an appropriate amount of the enzyme at 30° C. for 10 min. The reaction was then terminated by adding a TCA reaction terminating solution (0.5 ml) according to Tsai et al. (consisting of 110 mM trichloroacetic acid, 220 mM sodium acetate, and 330 mM acetic acid).

The enzyme activity was assayed by determining the amount of amino acid produced using the TNBS method and the HPLC method. In the TMBS method, 100 mM $Na_2B_4O_7$ (0.5 ml) was added to a sample solution containing amino acid (0.5 ml), 20 µl of 110 mM TNBS (trinitrobenzenesulfonic acid) was then added, and the resulting mixture was quickly stirred. After 5 min, 100 mM $NaH_2PO_4$ containing 1.5 mM $Na_2SO_3$ (2 ml) was added to the reaction mixture to terminate the color reaction, and the absorbance at 420 nm was measured. HPLC was performed by subjecting a sample solution containing amino acid to high-performance liquid chromatography using an ODS column (column, Wakosil II 5C18 (4.6 dia.×250 mm) (Wako Pure Chemical); eluent, $CH_3CN/50$ mM $KH_2PO_4 \cdot H_3PO_4$ (pH 2.5)=2:8; detection, A280 nm; and flow rate, 1.0 ml/min). The retention times were 3.5 min for D-tryptophan and 9.8 min for N-acetyl-D-tryptophan. Using D-tryptophan as the assay standard, one unit (or U) of the enzyme was defined as the amount of the enzyme required to produce 1 µmol of D-tryptophan at 30° C. for 1 min.

It was found that *Hypomyces mycophilus* IFO 6785 has a relatively high D-aminoacylase activity.

EXAMPLE 5

Purification of D-aminoacylase Derived from *Hypomyces mycophilus* IFO 6785 Strain 1. Conditions for D-aminoacylase Production This fungal strain was cultured in the YM liquid medium (50 ml) described in Example 4 supplemented with or without N-acetyl-DL-valine, N-acetyl-DL-tryptophan, N-acetyl-DL-methionine, DL-valine, DL-tryptophan, or DL-methionine (0.1% each) as the enzyme inducer at 25° C. for 96 h in a baffled Erlenmeyer flask on a rotary shaker (145 rpm). After incubation, a crude enzyme solution was prepared and assayed for enzyme activity by HPLC in the same manner as in Example 4. The results are shown in Table 4.

TABLE 4

| Inducer | pH | DCW* g/l-broth | Protein mg/ml | Activity units/ml | Activity units/mg |
|---|---|---|---|---|---|
| None | 5.02 | 5.188 | 0.248 | 0.00854 | 0.0345 |
|  | 5.12 | 1.925 | 0.771 | 0.0349 | 0.0453 |
| DL-Val | 5.08 | 3.100 | 0.854 | 0.0198 | 0.0232 |
|  | 4.88 | 5.025 | 1.520 | 0.0323 | 0.0213 |

TABLE 4-continued

| Inducer | pH | DCW* g/l-broth | Protein mg/ml | Activity units/ml | Activity units/mg |
|---|---|---|---|---|---|
| DL-Trp | 4.80 | 4.438 | 1.144 | 0.0213 | 0.0186 |
|  | 5.15 | 7.100 | 0.437 | 0.0118 | 0.0270 |
| DL-Met | 4.53 | 7.675 | 1.172 | 0.0283 | 0.0241 |
|  | 4.91 | 2.800 | 1.017 | 0.0241 | 0.0237 |
| N-Ac-DL-Val | 4.23 | 3.788 | 0.256 | 0.00468 | 0.0183 |
|  | 4.27 | 1.938 | 0.475 | 0.0103 | 0.0216 |
| N-Ac-DL-Trp | 4.44 | 7.688 | 0.497 | 0.00705 | 0.0142 |
|  | 4.51 | 3.013 | 1.101 | 0.0358 | 0.0325 |
| N-Ac-DL-Met | 4.31 | 1.975 | 0.520 | 0.0120 | 0.0231 |
|  | 4.35 | 3.913 | 0.795 | 0.0221 | 0.0278 |

*: DCW stands for the dry cell weight.

The results indicate that D-aminoacylase is not an inducible enzyme but a constitutive enzyme in this fungal strain.

2. Culturing Method Using Jar Fermentor

This fungal strain was cultured in 20 liters of a liquid medium (containing 0.3% yeast extract (Kyokuto Seiyaku), 0.3% malt extract (Kyokuto Seiyaku), 1.0% polypeptone (Wako Pure Chemical), 2.0% glucose (Wako Pure Chemical), and 0.01% silicon FS028; pH 6.0) then placed in a 30-1 jar fermentor at 25° C., 200 rpm, 1 v.v.m., without pressure for 44 h. The preculture used was obtained by the flask culture method in Example 4.

After culturing, the culture was immediately cooled in ice-water and filtered using No. 5A filter paper (Toyo Roshi) by suction to collect the fungal cells. The cells thus collected were washed with physiological saline solution, recovered again by the suction filtration, and stored at −90° C. till use.

(1) Cell Disruption, Removal of Nucleic Acid, and Salting out with Ammonium Sulfate Frozen cells (about 100 g) were wrapped in double-layered plastic bags with zippers and pulverized in an aluminum vat using a mallet. Pulverized cells were added to 50 mM Tris-HCl (pH 9.0) containing 1 μM leupeptin, 1 μM pepstatin A, 1 mM PMSF, and 0.01% 2-ME to prepare a cell suspension. The suspension was then subjected to continuous trituration with a Dyno mill type KDL (Wiley A. Bachofen, Based, Switzerland) using 0.2 to 0.5 mm glass beads.

The resulting cell triturate was centrifuged (with a Hitachi Koki centrifuge 20PR-52D using a RPR-9 rotor) at 8,000 rpm (6,000×g) at 4° C. for 30 min to sediment unbroken cells and cell debris. The supernatant thus obtained was assayed to determine the protein concentration according to the method described in Example 4. As a result, since the total protein amounted to 61,500 mg, ¹⁄₁₀th weight of protamine sulfate was added dropwise to the supernatant as a 3% solution (in the same buffer used for the trituration) with stirring at low temperature, and the mixture was stirred for an additional 2 h. The resulting mixture was centrifuged (with a Hitachi Koki centrifuge 20PR-52D using an RPR-9 rotor) at 6,000 rpm (3,000×g) for 20 min at 4° C. to sediment microsomes and nucleic acids.

The supernatant was reversely dialyzed against 17 liters of 50 mM Tris-HCl (pH 9.0) containing 77% saturated ammonium sulfate, 0.1 mM PMSF, 0.1 μM leupeptin, 0.1 μM pepstatin A, and 0.01% 2-ME with stirring overnight. Since this did not completely salt out D-aminoacylase, ammonium sulfate in excess to the dialyzate was added directly with stirring at low temperature. The precipitate was collected by centrifugation (with a Tomy Seiko RS-20BH centrifuge using a BH-9 rotor) at 10,000 rpm (16,000×g) at 4° C. for 20 min then suspended in a small amount of 10 mM Tris-HCl (pH 9.0) containing 0.1 mM PMSF, 0.1 μM leupeptin, 0.1 μM pepstatin A, and 0.01% 2-ME. The suspension was dialyzed against the same buffer (10 liter) for 4 h, and then against the same freshly replaced buffer (10 liter) overnight.

(2) DEAE-Sepharose FF 5.0/25 Anion Exchange Chromatography

The above-described enzyme thus prepared was further purified by anion exchange chromatography. Namely, the crude enzyme solution was adsorbed by an XK50 column (5.0 dia.×25 cm, 500 ml) packed with DEAE-Sepharose FF (both from Amersham Pharmacia Biotech) equilibrated with 10 mM Tris-HCl (pH 9.0) containing 0.01% 2-ME. After the column was washed with three volumes of the same buffer, the enzyme was eluted with a linear gradient of NaCl from 0 M to 0.5 M in seven volumes of the same buffer. The amount of protein in each fraction was estimated by measuring the absorbance at 280 nm (FIG. 1).

The D-aminoacylase activity was assayed by performing the enzyme reaction in 50 mM Tris-HCl (pH 7.5) containing 20 mM N-acetyl-D-tryptophan (total volume of 100 μl) at 30° C. for 30 min. An equal volume of 100 mM $Na_2B_4O7$—NaOH solution containing 4 mM TNBS was added to the above reaction mixture. The absorbance was measured at 450 nm to estimate the amount of free D-tryptophan.

D-Aminoacylase was eluted with a buffer containing from 0.20 to 0.25 M NaCl. Fractions containing the D-aminoacylase activity were combined, and concentrated fivefold using a UF membrane (Amicon, YM-10 76 mm dia.). Ammonium sulfate was added to the concentrate to 70% saturation, and the mixture was allowed to stand overnight to complete the precipitation. The mixture was then centrifuged (with a Hitachi Koki HIMAC CR26H centrifuge using a RR18A rotor) at 12,000 rpm (18,000×g) and 4° C. for 10 min to recover the precipitate. The recovered precipitate was suspended in 10 ml of 200 mM KPB (pH 8.5) containing 0.01% 2-ME and 0.3 M $Na_2SO_4$, dialyzed against the same buffer (2 liters) overnight. Dialysis was performed then again against the same but freshly replaced buffer (2 liters) for 4 h.

(3) Phenyl-Sepharose HP 2.6/10 Hydrophobic Chromatography

Figure 2:
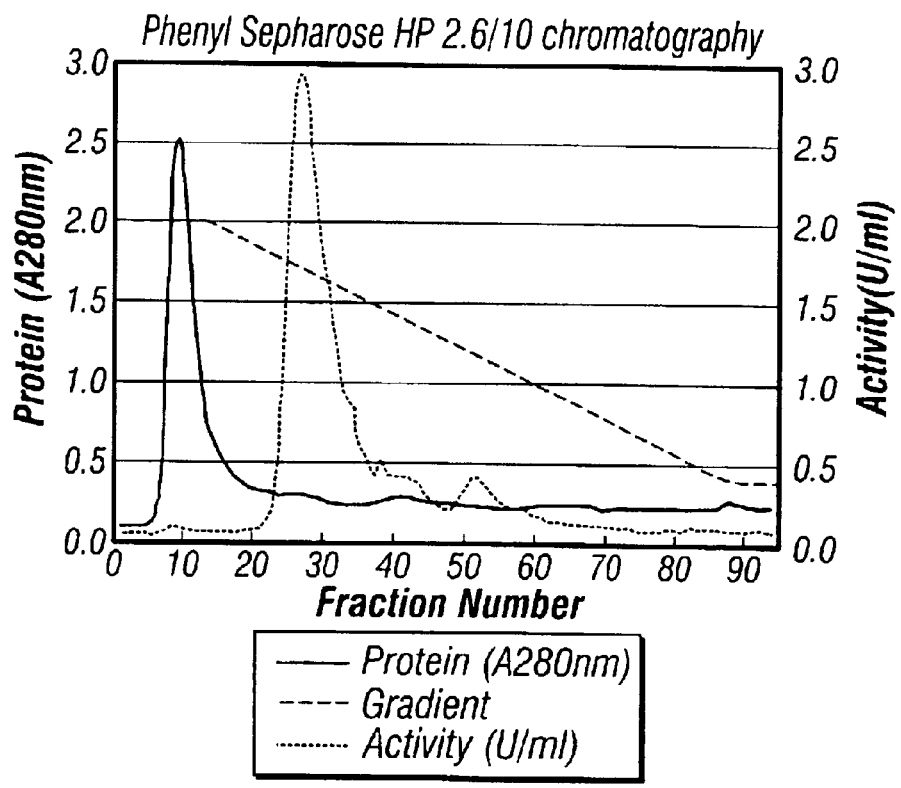
FIG. 2 shows the purification of the D-aminoacylase of the present invention by Phenyl-Sepharose Hi-Load HP 2.6/10 hydrophobic chromatography.

The enzyme obtained in (2) was further purified by hydrophobic chromatography. Specifically, the enzyme was adsorbed by a Phenyl-Sepharose Hi-Load HP2.6/10 column (Amersham Pharmacia Biotech, 2.6 dia. ×10 cm, 50 ml) equilibrated with 200 mM KPB (pH 8.5) containing 0.01% 2-ME and 0.3 M $Na_2SO_4^-$. After the column was washed with four volumes of the same buffer, the enzyme was eluted by linearly decreasing the concentration of $Na_2SO_4$ in the above-described buffer (buffer A) from 0.3 M to 0 M, that is, linearly increasing the concentration of 10 mM KPB (pH 8.5) containing 0.01% 2-ME from 0% to 100% in buffer A. The amount of protein in each fraction was estimated by measuring the absorbance at 280 nm. The D-aminoacylase activity was assayed in the same manner as described in (2) (FIG. 2).

Ammonium sulfate was added to the fractions containing the D-aminoacylase activity to 70% saturation, and the mixture was gently stirred for 2 h to form precipitates, which were recovered by centrifugation (with a Hitachi Koki HIMAC CR26H centrifuge using a RR18A rotor) at 12,000 rpm (18,000×g) and 4° C. for 10 min. The precipitate thus recovered was dissolved in about 3 ml of 10 mM Tris-HCl (pH 9.5) containing 0.01% 2-ME and 0.3 M NaCl.

(4) Superdex 200 Hi-Load 1.6/60 Gel Filtration Chromatography

Figure 3:
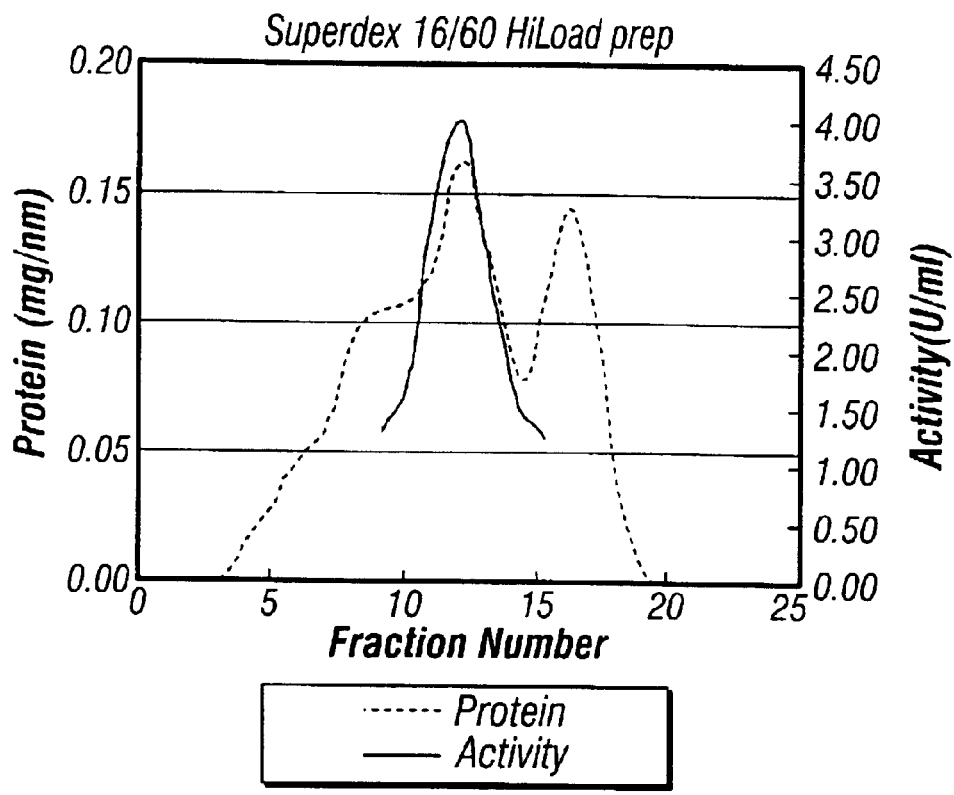
FIG. 3 shows the purification of the D-aminoacylase of the present invention by Superdex 200 Hi-Load 1.6/60 gel filtration chromatography.

The enzyme solution obtained in (3) was further purified by gel filtration chromatography. Specifically, the enzyme was applied onto a Superdex 200 Hi-Load 1.6/60 column (Amersham Pharmacia Biotech, 1.6 dia.×60 cm, 120 ml) equilibrated with 10 mM Tris-HCl (pH 9.5) containing 0.01% 2-ME and 0.3 M NaCl, and eluted with the same buffer (240 ml) at a flowrate of 1 ml/min. The amount of protein in each fraction was estimated by measuring the absorbance at 280 nm. The D-aminoacylase activity was assayed in the same manner as described in (2) (FIG. 3).

The fractions containing the D-aminoacylase activity were concentrated using a UF membrane (Amicon, YM-10, 43 mm dia.), diluted with 10 mM Tris-HCl (pH 9.5) containing 0.01% 2-ME, and concentrated again. The same procedure was repeated twice to desalt the sample.

(5) MonoQ HR 5/5 Anion Exchange Chromatography

The above-purified enzyme was further purified by anion exchange chromatography. Specifically, the enzyme was adsorbed by a MonoQ HR 5/5 column (Amersham Pharmacia Biotech, 0.5 dia. ×5 cm, 1.0 ml) equilibrated with 10 mM Tris-HCl (pH 9.0) containing 0.01% 2-ME. After the column was washed with three volumes of the same buffer, the enzyme was eluted with a linear gradient of NaCl from 0 M to 0.6 M in 21-volumes of the same buffer. The amount of protein in each fraction was estimated by measuring the absorbance at 280 nm.

The D-aminoacylase activity was assayed in the same manner as described in (2). A portion of the fraction having the D-aminoacylase activity was subjected to SDS-polyacrylamide gel electrophoresis (SDS-PAGE).

(6) SDS-polyacrylamide Gel Electrophoresis

Electrophoresis was performed using a Phast-System (Amersham Pharmacia Biotech) according to the method of Laemmli (Laemmli, U. K.: Nature, 227, pp680). A Phast gel Homo 12.5 (Amersham Pharmacia Biotech) was used as the gel. The sample for electrophoresis was prepared by mixing the enzyme solution with an equal volume of the sample treatment solution (125 mM Tris-HCl buffer (pH 6.8) containing 4% sodium dodecyl sulfate (SDS ), 20% glycerol, 10% 2-ME, and 0.005% Bromophenol Blue (BPB)); heating the mixture at 100° C. for about 5 min in a block heater; then cooling it to the room temperature. Aliquots (2 µl) were subjected to electrophoresis. The protein was detected by a staining method with CBB-R. As a result, only a unique single band presumed to be the desired D-aminoacylase was detected.

EXAMPLE 6

Property of D-aminoacylase Derived from
*Hypomyces mycophilus* IFO 6785 strain

1. Determination of Molecular Weight

Molecular weight was determined by (1) gel filtration and (2) SDS-polyacrylamide gel electrophoresis (SDS-PAGE).

(1) Gel Filtration

Figure 4:
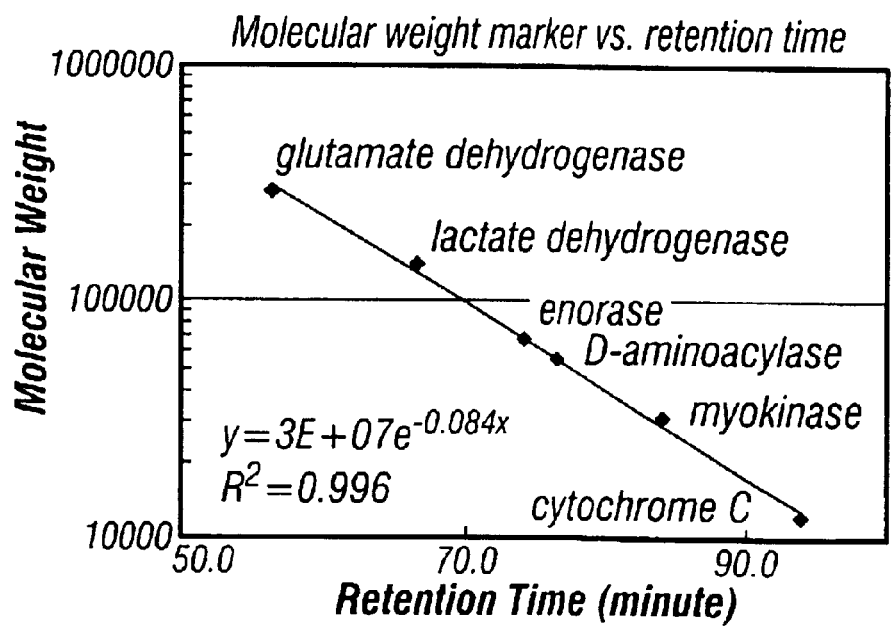
FIG. 4 shows the molecular weight of the D-aminoacylase of the present invention measured by Superdex 200 Hi-Load 1.6/60 gel filtration chromatography.

D-Aminoacylase derived from *Hypomyces mycophilus* IFO 6785 strain obtained in Example 2 was purified in the same manner as in Example 5 and subjected to the gel filtration as described in Example 5-3(4). MW-Marker proteins (HPLC) (Oriental Yeast) consisting of glutamate dehydrogenase (290,000), lactate dehydrogenase (142,000), enolase (67,000), myokinase (32,000), and cytochrome C (12, 400) were used as molecular weight markers. As a result, the molecular weight of this enzyme was indicated to be about 56,000 (FIG. 4).

(2) SDS-polyacrylamide Gel Electrophoresis

Figure 5:
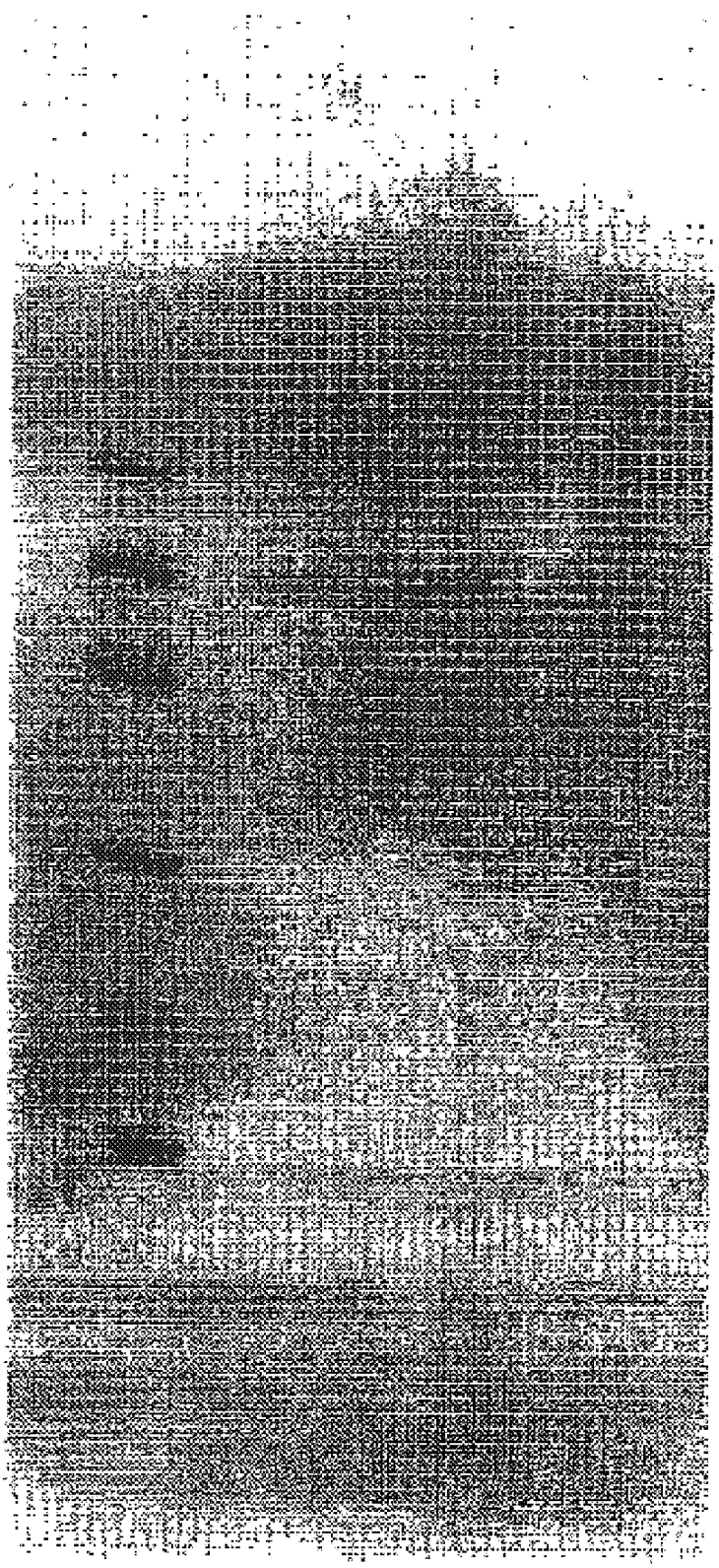
FIG. 5 shows the electrophoretogram of the D-aminoacylase of the present invention by SDS-PAGE.

D-Aminoacylase derived from *Hypomyces mycophilus* IFO 6785 strain in Example 2 was purified in the same manner as in Example 5 and subjected to electrophoresis as described in Example 5-3(6). An Electrophoresis Caribration Kit (Amersham Pharmacia Biotech) consisting of phosphorylase b (94,000), bovine serum albumin (67,000), ovalbumin (43,000), carbonic anhydrase (30,000), soybean trypsin inhibitor (20,100), and α-lactoalbumin (14,400) provided the molecular weight markers. As a result, the molecular weight of this enzyme was indicated to be about 64,000 (FIG. 5).

2. Substrate Specificity

Substrate specificity of the enzyme was expressed as the percentage of the specific activity compared with that for N-acetyl-D-methionine taken as 100%. N-chloroacetyl-D-phenylalanine, N-acetyl-D-valine, N-acetyl-D-phenylalanine, N-acetyl-D-tryptophan, N-acetyl-D-leucine, N-acetyl-L-valine, N-acetyl-L-phenylalanine, N-acetyl-L-tryptophan, and N-acetyl-L-leucine substrates were used for the comparison. The enzyme reaction was performed in 50 mM Tris-HCl (pH 7.5) containing 1 µl of the enzyme solution and 20 mM of each substrate (total volume 1.0 ml) at 30° C. for 20 min, and terminated by adding 0.5 ml of a TCA reaction terminating solution according to Tsai et al. (consisting of 110 mM trichloroacetic acid, 220 mM sodium acetate, and 330 mM acetic acid). The enzyme activity was assayed by the TNBS method as described in Example 4(2). The results are shown in Table 5.

TABLE 5

|  | D-enantiomer | L-enantiomer |
|---|---|---|
| N-Acetyl-amino acid | | |
| Phe | 298 | 0 |
| Trp | 109 | 0 |
| Met | 100 | 0 |
| Leu | 77.5 | 0 |
| Val | 17.5 | 0 |
| Ala | 0 | |
| Asn | 0 | |
| Ile | 0 | |
| Pro | 0 | |
| Penicillin | 0 | |
| N-Chloroacetyl-amino acid | | |
| Phe | 708 | |
| N-Benzoyl-amino acid | | |
| Phe | 0 | |

As indicated in the table, this enzyme was especially active for N-acetyl-D-phenylalanine and N-chloroacetyl-D-phenylalanine, very active for N-acetyl-D-tryptophan, N-acetyl-D-methionine and N-acetyl-D-leucine, and somewhat active for N-acetyl-D-valine, but inactive for N-acetyl-L-phenylalanine, N-acetyl-L-tryptophan, N-acetyl-L-methionine, N-acetyl-L-valine, and N-acetyl-L-leucine.

3. Optimal pH

Figure 6:
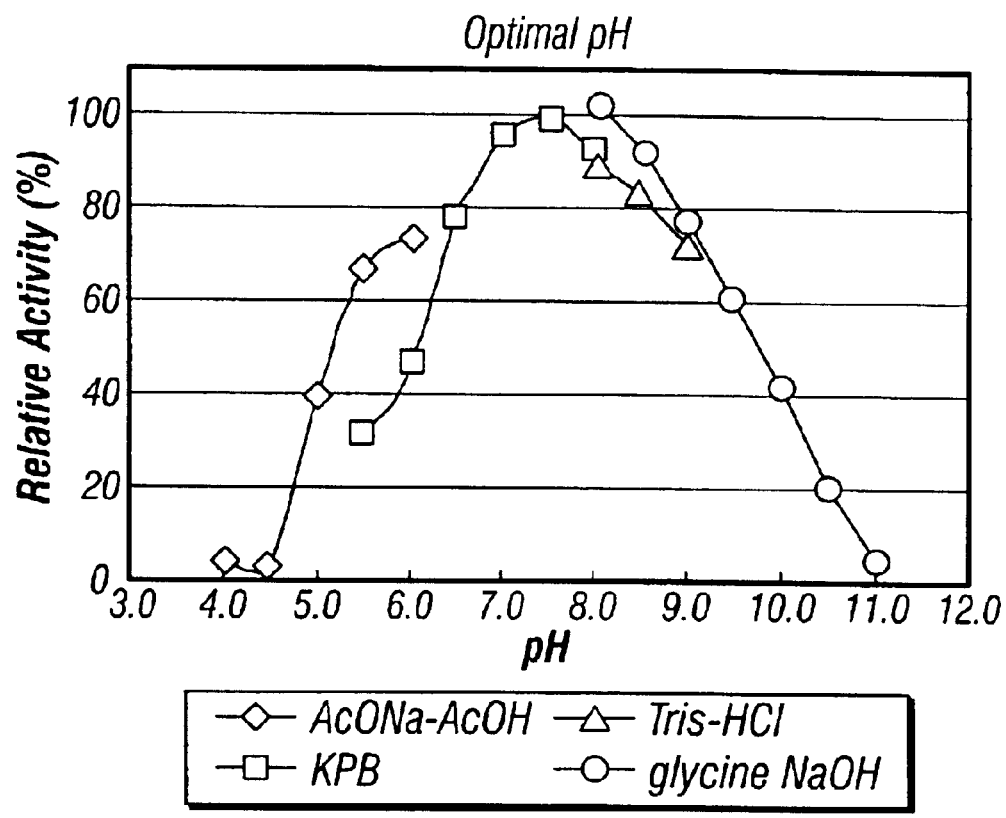
FIG. 6 shows the optimal pH for the reactivity of the D-aminoacylase of the present invention. Black diamond indicates the enzyme activity in AcONa.AcOH; black square, the activity in $K_2HPO_4$. $KH_2PO_4$; black triangle, the activity in Tris-HCl; and black circle the activity in glycine NaOH.

Enzyme assay was performed at 30° C. for 5 min according to the method described in Example 4(2) varying the pH of the enzyme reaction system from pH 4.0 to pH 11.0. The amount of enzyme was determined by HPLC as described in Example 4(2). The buffers used were 50 mM AcONa. AcOH buffer for pH 4.0 to 6.0, 50 mM $K_2HPO_4$. $KH_2PO_4$ buffer for pH 5.5 to 8.0, 50 mM Tris-HCl buffer for pH 7.0 to 9.0, and 50 mM glycine. NaOH buffer for pH 8.0 to 11.0. The results are shown in FIG. 6. The results indicated that the optimal pH for the reaction of this enzyme was from 7.5 to 8.0 and that the enzyme exhibits not less than 80% of its activity within the pH range from 6.5 to 9.0.

4. Optimal Temperature

Figure 7:
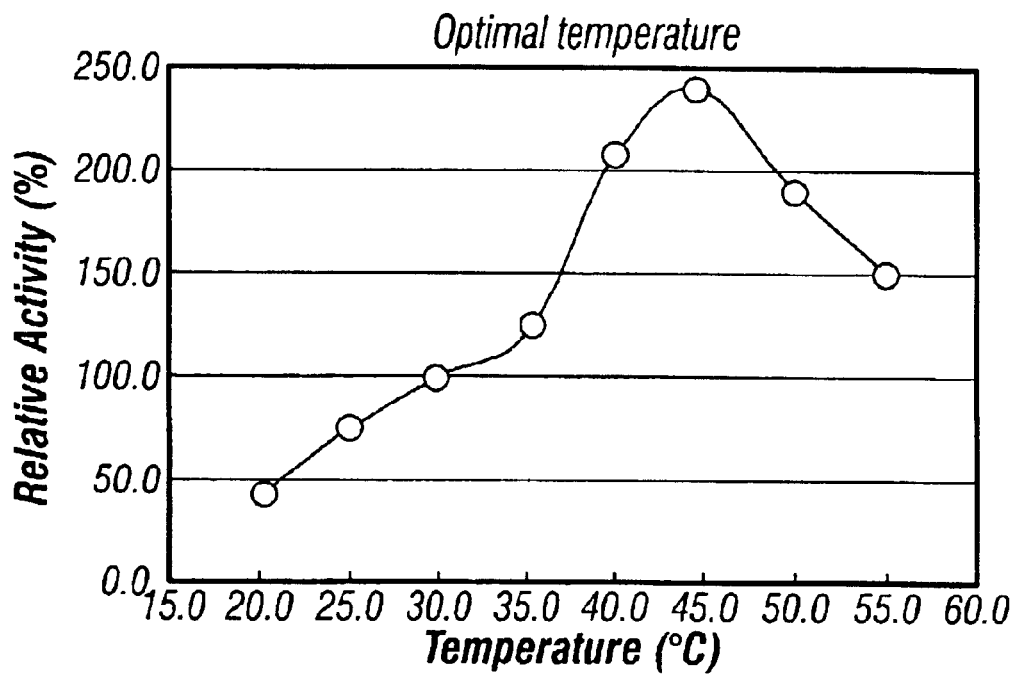
FIG. 7 shows the optimal temperature for the reactivity of the D-aminoacylase of the present invention.

Enzyme assay was performed for 5 min according to the method described in Example 4(2) while varying the temperature of the enzyme reaction system from 20° C. to 55° C. The enzyme was determined by HPLC as described in Example 4(2). In order to prevent a temperature-dependent pH change, 50 mM $K_2.HPO_4$ $KH_2PO_4$ buffer (pH 7.5) was used. The results are shown in FIG. 7. The results indicated that the optimal temperature for reaction of this enzyme was about 45° C.

5. pH Stability

Figure 8:
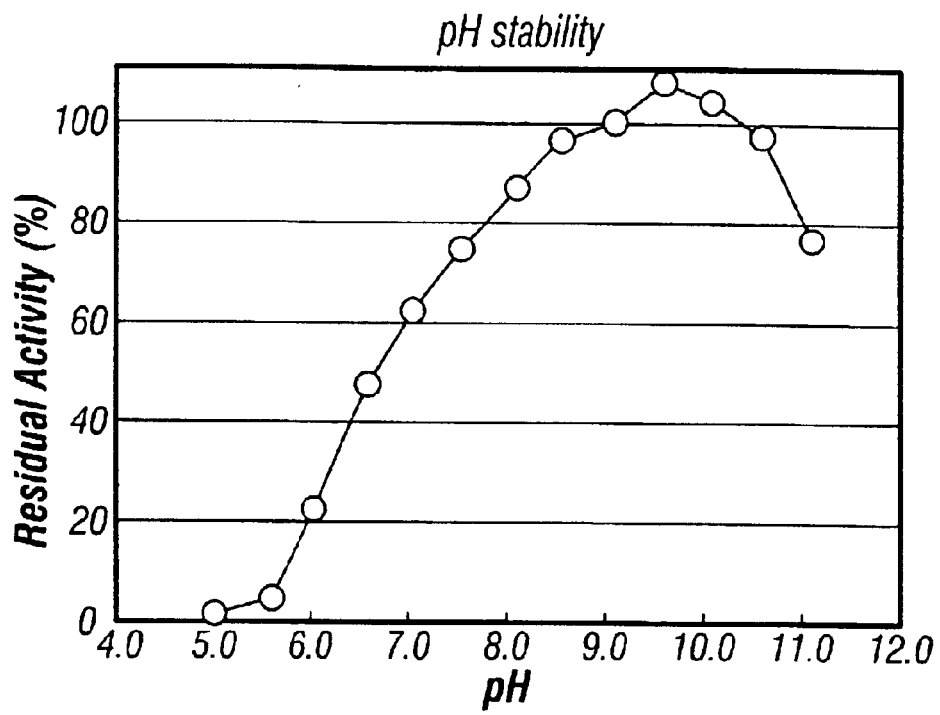
FIG. 8 shows pH stability of the D-aminoacylase of the present invention.

The enzyme solution was diluted 50-fold with each pH buffer, kept at 30° C. for 30 min, thoroughly cooled in ice, and then assayed for the residual enzyme activity according to the method described in Example 4(2). The enzyme was determined by HPLC as described in Example 4(2). In order-to minimize the influence of buffer constituents, Britton and Robinson's buffer (Basal Methods of Protein and Enzyme Experiments, 2nd Rev. Ed., Buichi Horio ed., 1994) containing 0.01% 2-ME was used, changing pH from 5.0 to 11.0 at 0.5 intervals. The results are shown in FIG. 8 and revealed that this enzyme was most stable at pH 9.5, expressing not less than 80% of its activity within the pH range from pH 7.5 to 10.5.

6. Thermostability

Figure 9:
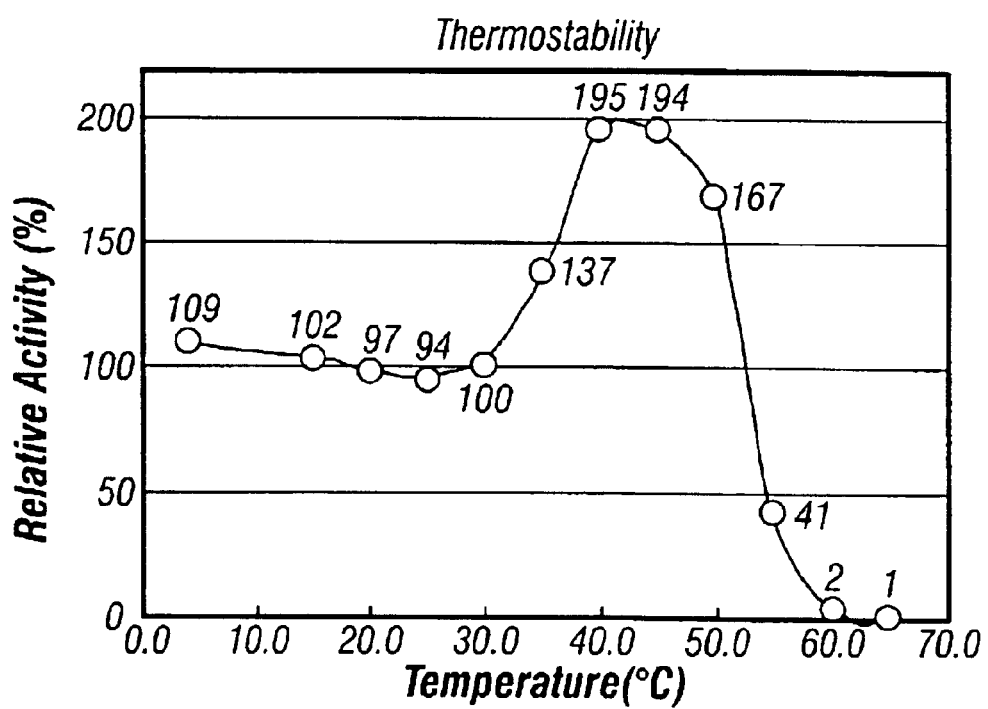
FIG. 9 shows thermostability of the D-aminoacylase of the present invention.

The enzyme solution was diluted with the buffer, kept at each temperature from 15 to 60° C. for 30 min, thoroughly cooled in ice, and then assayed for the residual enzyme activity according to the method described in Example 4(2). The enzyme was determined by HPLC as described in Example 4(2). Britton and Robinson's buffer (pH 9.5) containing 0.01% 2-ME was used as the buffer. The diluted enzyme solution was either not treated (kept at 4° C.) or treated at each temperature from 15° C. to 65° C. at 5° C. intervals. The results shown in FIG. 9 indicate that this enzyme was activated by heating to 40° C. to 45° C., but quickly inactivated when heated to 50° C. or higher. The enzyme was also effectively activated by heating at 40° C. for 30 min. Both longer and shorter heating periods were less effective, and once activated, enzyme maintained its activity for about 3 days when stored at 4° C.

7. Effects of Various Metal Salts and Reagents

The enzyme solution was diluted with Britton and Robinson's buffer (pH 9.5) containing 1 mM DTT, activated by heating at 40° C. for 30 min, diluted with the same buffer containing various metal salts and reagents, and kept at 40° C. for 30 min. After cooling sufficiently, the mixture was assayed for the residual enzyme activity according to the method described in Example 4 (2). The amount of enzyme was determined by HPLC as described in Example 4 (2). The results are shown in Tables 6 and 7.

TABLE 6

| Metal ion | Concentration (mM) | Relative activity (%) |
|---|---|---|
| KCl | 1 | 102 |
| $MgCl_2$ | 1 | 98.0 |
| $CaCl_2$ | 1 | 104 |
| $ZnCl_2$ | 1 | 26.2 |
| $NiCl_2$ | 1 | 57.7 |
| $CoCl_2$ | 1 | 63.1 |
| $MnCl_2$ | 1 | 100 |
| No addition | | 100 |

TABLE 7

| Compound | Action | Concentration (mM) | Relative activity (%) |
|---|---|---|---|
| Hydroxylamine | Carbonyl reagent | 1 | 96.2 |
| Iodoacetamide | SH-enzyme | 1 | 185 |
| N-ethylmaleimide | SH-enzyme | 1 | 15.2 |
| Sodium azide | Respiratory chain inhibitor | 1 | 90.9 |
| P-Chloromercuri-benzoic acid | SH-enzyme | 0.5 | 99.6 |
| $HgCl_2$ | SH-enzyme | 0.01 | 13.4 |
| $CuSO_4$ | SH-enzyme | 1 | 20.4 |
| $ZnSO_4$ | SH-enzyme | 1 | 11.6 |
| o-Phenanthroline | metal enzyme | 1 | 78.8 |
| EDTA | metal enzyme | 1 | 96.0 |
| EGTA | metal ion | 1 | 90.9 |
| PMSF | serine protease or choline esterase | 1 | 94.2 |
| No addition | | — | 100 |

These data show that this enzyme was inhibited by metal ions such as $Co^{2+}$, $Cu^{2+}$, $Zn^{2+}$ and $Hg^{2+}$ but also exhibited previously unknown properties such as not being inhibited by EDTA and being activated by $ICH_2CONH_2$.

8. Determination of Internal Sequence

A solution containing the purified enzyme (1 nmol) was concentrated by ultrafiltration to 50 μl, 50 mM Tris-HCl (pH 9.0) containing 8 M urea (150 μl) was added to the concentrated solution, and the mixture was kept at 37° C. for 1 h. After 200 μl of 50 mM Tris-HCl (pH 9.0) was added, the mixture was digested with lysyl endopeptidase (5 pmol) at 30° C. overnight. Digested products were fractionated by high-performance liquid chromatography using an ODS column (column, TSK gel ODS-120T (4.6dia.×250 mm) (Tosoh); eluent, buffer A (0.1% TFA) and buffer B (80% $CH_3CN$ containing 0.095% TFA); detection, 214 nm; flow rate, 1.0 ml/min; eluted by a programmed gradient), and fractions were recovered.

The resulting fractions were concentrated by a centrifugal evaporator (UNISCIENCE, UNIVAP) and sequenced with a protein sequencer (A477, Applied Biosystems). Partial amino acid sequences thus determined are shown in SEQ ID Nos: 1 through 5.

What is claimed is:

1. An isolated D-aminoacylase comprising SEQ ID NO:1, SEQ ID NO:2, SEQ ID NO:3, SEQ ID NO:4, and SEQ ID NO:5, wherein said D-aminoacylase is derived from a fungus belonging to the genus *Hypomyces*.

2. The D-aminoacylase according to claim 1, wherein said fungus belongs to a species selected from the group consisting of *Hypomyces aurantius, Hypomyces broomeanus, Hypomyces chrysospermus, Hypomyces rosellus, Hypomyces sepulcralis, Hypomyces subiculosus, Hypomyces mycophilus*.

3. The D-aminoacylase according to claim 2, wherein said fungus is a strain selected from the group consisting of *Hypomyces aurantius* IFO 6847, *Hypomyces broomeanus* IFO 9164, *Hypomyces rosellus* IFO 6911, *Hypomyces chrysospermus* IFO 6817, *Hypomyces sepulcralis* IFO 9102, *Hypomyces subiculosus* IFO 6892, *Hypomyces mycophilus* ATCC 76474 or IFO 6785.

4. An isolated D-aminoacylase comprising SEQ ID NO: 1, SEQ ID NO:2, SEQ ID NO:3, SEQ ID NO:4 and SEQ ID NO:5, wherein said D-aminoacylase catalyzes the synthesis of a D-amino acid from a corresponding N-acetyl-D-amino acid, and wherein said D-aminoacylase has a molecular weight of about 64,000 daltons by SDS-polyacrylamide gel electrophoresis and about 56,000 daltons by gel filtration chromatography, and wherein the D-aminoacylase is a fungal enzyme.

5. The D-aminoacylase of claim 4, wherein the N-acetyl-D-amino acid is selected from the group consisting of N-acetyl-D-tryptophan, N-acetyl-D-phenylalanine, N-acetyl-D-valine, N-acetyl-D-leucine or N-acetyl-D-methionine.

6. The D-aminoacylase of claim 4, wherein the D-aminoacylase is stabilized by reducing agents.

7. The D-aminoacylase of claim 4, where the D-aminoacylase is activated by ICH2CONH2.

8. The D-aminoacylase of claim 4, wherein the D-aminoacylase is stable at 40° C. for at least 30 minutes at pH 9.5.

9. The D-aminoacylase of claim 4, wherein the D-aminoacylase is stable at 45° C. for at least 30 minutes at pH 9.5.

10. The D-aminoacylase of claim 4, wherein the D-aminoacylase is inactivated at a temperature above 60° C. for about 30 minutes at about pH 9.5.

11. The D-aminoacylase of claim 4, wherein at pH 7.5 the D-aminoacylase has an optimal temperature of about 45° C.

* * * * *

UNITED STATES PATENT AND TRADEMARK OFFICE
CERTIFICATE OF CORRECTION

PATENT NO.   : 6,905,861 B2
DATED        : June 14, 2005
INVENTOR(S)  : Kazuya Mitsuhashi et al.

It is certified that error appears in the above-identified patent and that said Letters Patent is hereby corrected as shown below:

Title page,
Item [*] Notice, add -- This patent is subject to terminal disclaimer --.

Column 23,
Line 13, delete "ICH2CONH2" and insert -- ICH$_2$CONH$_2$ --.

Signed and Sealed this

Twenty-fourth Day of January, 2006

JON W. DUDAS
*Director of the United States Patent and Trademark Office*